United States Patent [19]

Kulis

[11] Patent Number: 4,637,159
[45] Date of Patent: Jan. 20, 1987

[54] ARTIFICIAL EYE

[76] Inventor: Joseph E. Kulis, 280 Grand Blvd., Beford, Ohio 44146

[21] Appl. No.: 792,058

[22] Filed: Oct. 28, 1985

[51] Int. Cl.$^4$ .............................................. A61F 1/16
[52] U.S. Cl. ...................................... 43/42.32; 623/4; 446/389; 446/392
[58] Field of Search ................. 43/42.33, 42.34, 42.32; 446/389, 392; 623/4

[56] References Cited

U.S. PATENT DOCUMENTS

| | | | |
|---|---|---|---|
| 1,337,354 | 4/1920 | Garrigue | 43/42.32 X |
| 1,445,481 | 2/1923 | Buckler . | |
| 1,738,192 | 12/1929 | Marcus . | |
| 1,740,675 | 12/1929 | Wilhelm . | |
| 1,832,743 | 11/1931 | Shuldiner | 446/392 |
| 1,963,129 | 6/1934 | Grubman . | |
| 2,820,325 | 1/1958 | Prupis . | |
| 3,480,971 | 12/1969 | Smith | 623/4 |
| 3,952,445 | 4/1976 | Liebert . | |

FOREIGN PATENT DOCUMENTS

| | | |
|---|---|---|
| 178457 | 5/1954 | Austria . |
| 692389 | 11/1930 | France . |
| 712048 | 9/1931 | France . |
| 1167246 | 11/1958 | France . |
| 415884 | 11/1947 | Italy ............................ 446/392 |

OTHER PUBLICATIONS

Van Dyke Catalog, pp. 84, 85, 91, 93, 94.
Jonas Bros. Catalog, pp. 15, 16.

Primary Examiner—Nicholas P. Godici
Assistant Examiner—Carmine Cuda
Attorney, Agent, or Firm—Fay, Sharpe, Fagan, Minnich & McKee

[57] ABSTRACT

A simulated eye construction includes a generally cup-shaped member including a protruding transparent first lens portion having a convex outer face and, preferably, a concave inner face which can be provided with a recessed portion. A transparent second lens member is positioned in the cup-shaped member behind the first lens portion. A reflecting structure is positioned behind the second lens member for reflecting at least some of the light entering the first and second lens members back through them. A closure structure is provided for closing the open end of the cup-shaped member. A holding structure is provided for holding the second lens in place in the cup-shaped member.

18 Claims, 6 Drawing Figures

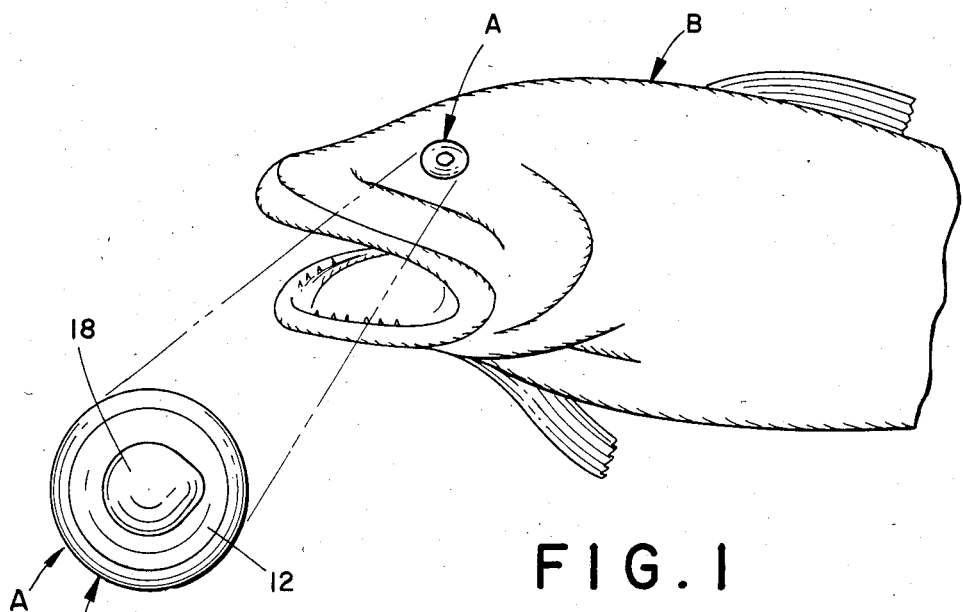
FIG. 1
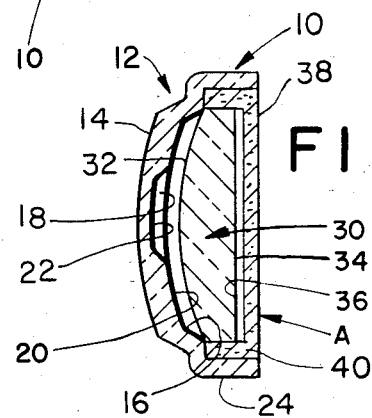
FIG. 2
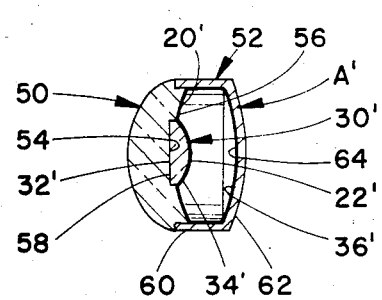
FIG. 3
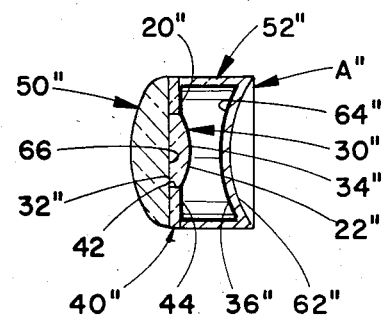
FIG. 4
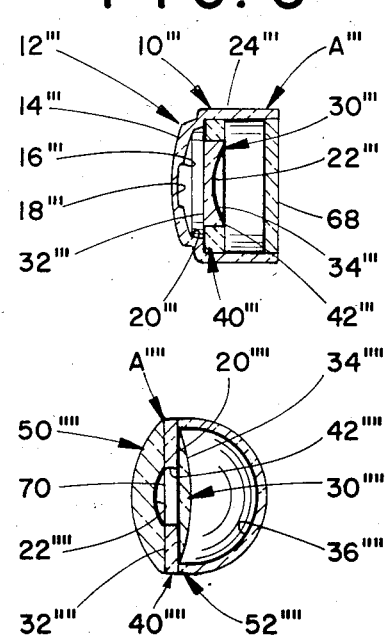
FIG. 5
FIG. 6

ARTIFICIAL EYE

BACKGROUND OF THE INVENTION

This invention generally pertains to artificial eyes. More specifically, the present invention relates to an artificial eye particularly intended for use in taxidermy.

The invention is specifically applicable to artificial fish eyes, such as walleye eyes, and will be described with particular reference thereto. However, it will be appreciated by those skilled in the art that the invention has broader applications and may also be adapted for taxidermy use for the eyes of other animals. Moreover, the invention can also be used as an artificial eye on fishing lures for game fish as well as other similar uses.

Heretofore, conventional artificial fish eyes provided for taxidermy purposes looked particularly unrealistic. Fish eyes generally have a teardrop-shaped pupil which can be black or, in the case of the walleye type of fish, a whitish color. The "walleye" (Stizostedium vitreum), also called the walleye pike, is a North American freshwater food and game fish known for its large, conspicuous eyes. The conventional artificial eyes used in the mounting of walleyes have a flat white pupil which has a milky color and looks quite unrealistic. In general, the use of inexpensive artificial eyes results in an expressionless mount since the eyes of the fish do not have the intricate details characteristic of a natural eye.

Accordingly, it has been considered desirable to develop a new and improved artificial eye construction which would overcome the foregoing difficulties and others while providing better and more advantageous overall results.

BRIEF SUMMARY OF THE INVENTION

In accordance with the present invention, a new and improved simulated eye construction is provided.

More particularly in accordance with the invention, the eye construction comprises a generally cup-shaped member including a protruding transparent first lens portion having a convex outer face. A transparent second lens member is positioned in the cup-shaped member behind the first lens portion. Reflecting means are positioned behind the second lens member for reflecting at least some of the light entering the first and second lens members back through them. Closure means are provided for closing the open end of the cup-shaped member and holding means are provided for holding the second lens in place in the cup-shaped member.

In accordance with another aspect of the invention, a simulated eye construction is provided.

According to this aspect of the invention, the eye construction includes a generally cup-shaped body having an inner cavity provided with a light reflecting surface. A transparent lens member, having a convex outer face and an inner face, is secured to the body at the entrance thereof to close the cavity. A first coating layer of a first color is provided on an inner face of the lens around the periphery thereof in order to simulate the iris of the eye. A second coating layer of a second color is provided on the lens inner face radially inwardly of the first layer to simulate the pupil of the eye. The second coating layer is translucent to allow light to penetrate the lens member and be reflected off the body light reflecting surface.

In accordance with another aspect of the invention, a simulated eye construction is provided.

According to this aspect of the invention, a first lens member and a body means for holding the first lens member are provided. A second lens member is held in the body means. Reflecting means, positioned in the body means behind the second lens member, is provided for reflecting at least some of the light entering the first and second lens members back through them. A first coating layer of a first color is provided on a surface of the first lens member. A second coating layer of a second color is provided on a surface of the second lens member. The second coating layer is translucent to allow light to penetrate the first and second lens members and be reflected off the reflecting means.

One advantage of the present invention is the provision of a new simulated eye construction which is more life-like and realistic than previous constructions since it provides a deep light reflecting pupil.

Another advantage of the invention is the provision of an eye construction which includes a body means in the form of a generally cup-shaped member having a protruding transparent first lens portion. A transparent second lens member is positioned in the cup-shaped member behind the first lens portion.

A further advantage of the invention is the provision of a protruding transparent firstt lens portion which includes a convex outer face and a concave inner face which is provided with a recessed portion of the same teardrop-shape as the pupil of the eye of a fish.

A still further advantage of the invention is the provision of a simulated eye construction which includes reflecting means positioned behind the lens member or members of the construction to reflect at least some of the light entering the construction back through the one or more lens members thereby providing a deep light reflecting eye construction.

A yet further advantage of the invention is the provision of a simulated eye construction having a body means in the form of a cup-shaped member including a first lens portion and a second lens member positioned in the cup-shaped member. Holding means are provided for holding the second lens in place in the cup-shaped member or body. The holding means can be a layer of putty material provided around the side edge of the second lens member. Alternatively, the holding means can be a disc-shaped member having a centrally disposed aperture. The second lens member is secured to the disc-shaped member in a relationship overlying the centrally disposed aperture thereof.

Still another advantage of the present invention is the provision of a simulated eye construction having a body means in the form of a cup-shaped body, reflecting means in the form of a light reflecting inner surface on the body and at least one lens member secured to the body. A first coating layer of a first color is provided around the periphery of the lens member and a second coating layer of a translucent second color is provided inwardly of the first layer to allow light to penetrate the at least one lens member and be reflected off the body light reflecting surface and back through the eye so that the eye can appear to have depth.

Yet another advantage of the present invention is the provision of a cup-shaped member which can have a rear surface which is convex, concave, or planar, as desired.

Yet still another advantage of the present invention is the provision of a simulated eye construction having a body means, and first and second lens members in which the second lens member is positioned within or adjacent to an apertured disc or wafer held in the body means.

Still other benefits and advantages of the invention will become apparent to those skilled in the art upon a reading and understanding of the following detailed specification.

BRIEF DESCRIPTION OF THE DRAWINGS

The invention may take physical form in certain parts and arrangements of parts, preferred embodiments of which will be described in detail in this specification and illustrated in the accompanying drawings which form a part hereof and wherein:

FIG. 1 is a perspective view of a portion of a mounted fish utilizing the simulated eye construction according to the present invention;

FIG. 2 is a side elevational view in cross section of a first preferred embodiment of the simulated eye construction according to the present invention;

FIG. 3 is a side elevational view in cross section of a second preferred embodiment of the simulated eye construction according to the present invention;

FIG. 4 is a side elevational view in cross section of a third preferred embodiment of a simulated eye construction according to the present invention;

FIG. 5 is a side elevational view in cross section of a fourth preferred embodiment of a simulated eye construction according to the present invention; and, FIG. 6 is a side elevational view in cross section of a fifth preferred embodiment of a simulated eye construction according to the present invention.

DETAILED DESCRIPTION OF THE PREFERRED EMBODIMENTS

Referring now to the drawings, wherein the showings are for purposes of illustrating preferred embodiments of the invention only and not for purposes of limiting same, FIG. 1 shows the subject new simulated eye construction A being positioned in a mounted fish B. While the simulated eye construction A is primarily designed for and will hereinafter be described in connection with taxidermy applications for fish, it should be recognized that the eye construction may also be useful in taxidermy applications for mammals or in other environments. While the construction is particularly applicable to walleyes, it is evident that other types of fish may be mounted using a similar type of eye construction. The walleye eye is particularly noted for the fact that its pupil portion is translucent or white instead of being black as with the eyes of most other fish and most types of mammals.

More particularly, in order to mount the fish B, which can be a walleye, the eyes thereof have to be removed and be replaced with an artificial eye construction. The eye construction A according to the present invention provides a deep light reflecting pupil which makes the eye of the fish B much more life-like and realistic than previous constructions which provided only a flat white pupil.

In order to obtain a deep light reflecting pupil according to a first preferred embodiment of the present invention, and with reference now to FIG. 2, a body means in the form of a cup-shaped member 10 is provided with a protruding transparent first lens portion 12. The lens portion 12 has a convex outer face 14 and a concave inner face 16 provided with a teardrop-shaped recessed portion 18 simulating the pupil of the eye of the fish B. A first coating layer 20, of a first color, is provided around the periphery of the concave inner face 16 of the first lens portion 12 and a second coating layer 22 of a second, contrasting, translucent color is provided within the recessed portion 18. Preferably, the second coating layer 22 has a translucent whitish color and the first coating layer 20 is a gold color, flecked with brown. The second coating layer 22 simulates the pupil of the walleye's eye and the first coating layer 18 simulates the iris of the walleye's eye.

As mentioned, the lens portion 12 is integral with the cup-shaped member 10 which also includes a cylindrical side wall portion 24 having a larger diameter than the first lens portion 12. Positioned within the cup-shaped member 10 is a second lens member 30 which can have a convex forward face 32 and a flat rear face 34. Provided on the rear face 34 is a reflecting means in the form of a reflecting layer 36 which reflects at least some of the light entering through the first and second lenses 12, 30 back out through the lenses.

Also provided in this embodiment is a clsure means 38 in the form of a putty material for closing the open end of the cup-shaped member 10. A layer of the putty around the side edge of the second lens 30 can also serve as a holding means 40 for holding the second lens 30 in place in the cup-shaped member 10.

The cup-shaped member 10 can be made out of a transparent material, such as glass, or some forms of plastics. The second lens 30 can, similarly, be made from glass or plastic.

With reference now to the second preferred embodiment illustrated FIG. 3, the invention is there shown in a different type of arrangement. For ease of illustration and appreciation of this alternative, like components are identified by like numerals with a primed (') suffix and new components are identified by new numerals.

In this FIGURE, the eye construction A' includes a first lens member 50, a body means in the form of a cup-shaped member 52 as well as a second lens member 30'. A cut out portion 54 is provided on a rear surface 56 of the first lens member 50 such that the second, and smaller diameter, lens member 30' may be positioned therein. The second lens member can have a convex inner surface 34' and a flat outer surface 32' which mates with a substantially flat surface 58 provided for the cut out portion 54 in the first lens 50. A first coating layer 20' of a first color is provided on the concave rear face 58 of the first lens 50 around the cut out portion 54. A second coating layer 22' of a second, translucent whitish color is provided on the convex inner surface 34' of the second lens 30'. The cup-shaped member 52 is provided with a cylindrical side wall portion 60 and a rear face 62 which can be concave. An inner surface 64 of the rear face 62 has coated thereon a reflecting means in the form of a shiny inner surface 36' to reflect light.

With reference now to the third preferred embodiment of FIG. 4, the invention is there shown as having still another construction. For ease of illustration and appreciation of this alternative, like components are identified by like numerals with a double primed (") suffix and new components are identified by new numerals.

In this FIGURE, the eye construction A" includes a first lens member 50", a cup-shaped member 52", a second lens member 30" and a holding means in the form of an apertured wafer or disc 40". The disc can be sized to have the same diameter as the cup-shaped member 51" and thus sit on the open end thereof. The second lens 30" is adapted to be positioned in an aperture 42 of the disc 40″. The aperture of the disc and the lens can be suitably shaped so that they have the teardrop appearance of the pupil of a fish eye. The second lens 30″ can have a flat outer surface 32″ which is positioned against a flat rear surface 66 of the first lens member 50″. The disc 40″ can be made of a transparent material such that a rear surface 44 of the disc can be provided with a colored layer 20″ of a first color. A translucent layer 22″ of a second, contrasting, color can be provided on the convex inner surface 34″ of the second lens 30″. In this embodiment, the cup member 52″ is provided with a convex rear face 62″ which is coated on its inner surface 64″ with a reflecting means in the form of shiny inner surface layer 36″.

With reference now to the fourth preferred embodiment of FIG. 5, the invention is there shown as having yet another construction. For ease of illustration and appreciation of this alternative, like components are identified by like numerals with a triple primed (‴) suffix and new components are identified by new numerals.

In this FIGURE, the eye construction includes a cup-shaped member 10‴, including a first lens portion 12‴, a second lens member 30‴ and a disc member 40‴. In this construction, the first lens portion 12‴ has a convex outer surface 14‴ and a concave inner surface 16‴ in which is provided a recessed portion 18‴. Also, in this construction, the cup-shaped member 10‴ includes a cylindrical side wall portion 24‴. The open end of the member 10‴ is closed by closure means in the form of a suitably sized mirror 68 which is suitably secured to the cup-shaped member. In this embodiment, the disc 40‴ can fit within the cylindrical side wall portion 24‴. With regard to this embodiment, a first coating layer 20‴ is provided on the exterior surface of the disc 40‴ since the disc is made of a non-transparent or opaque material rather than of a transparent or translucent material such as glass or plastic. The second lens 30‴ is positioned in an aperture 42″40 of the disc. Also, in this embodiment, the second lens 30‴ has a concave inner face 34‴ and a flat outer face 32‴. A translucent layer 22‴ coats one of the faces of the second lens 30‴.

With reference now to the final preferred embodiment of FIG. 6, the invention is there shown in yet still another construction. For ease of illustration and appreciation of this alternative, like components are identified by like numerals with a quadruple primed (″″) suffix and new components are identified by new numerals.

In this FIGURE, the simulated eye construction includes a first lens member 50″″, a cup-shaped member 52″″, a second lens member 30″″ and a disc member 40″″. The second lens member 30″″ fits within the front opening of the cup-shaped member 52″″ and the disc 40″″ fits over the cup-shaped member. The first lens 50″″ is secured over the front surface of the disc 40″″. A teardrop-shaped recessed portion 70 is provided on the inner surface of the first lens member 50″″. The second lens 30″″ is provided with a convex inner face 34″″ and a flat outer face 32″″ which is positioned adjacent an inner face of the disc member 40″″. The second lens 30″″ is secured to the disc 40″″ in a relationship overlying the centrally disposed aperture 42″″ thereof. The cup member 52″″ is provided with a shiny inner surface 36″″ to reflect back through the first lens at least some of the light entering through the two lenses 50″″ and 30″″. As with the other embodiments, first and second coating layers 20″″ and 22″″ are also provided.

The subject invention thus provides an artificial eye for taxidermy purposes or the like. The eye is particularly adapted for the mounting of fish such as walleye and provides a bright and shiny, deep, light reflecting pupil for the eye of the mounted fish.

The invention has been described with reference to preferred embodiments. Obviously, modifications and alterations will occur to others upon and the reading and understanding of this specification. It is intended to include all such alterations and modifications insofar as they come within the scope of the appended claims or the equivalents thereof.

Having thus described the invention, it is now claimed:

1. A simulated eye construction comprising:
    a generally cup-shaped member including a protruding transparent first lens portion having a convex outer face;
    a transparent second lens member positioned in said cup-shaped member behind said first lens portion;
    reflecting means positioned behind said second lens member for reflecting at least some of the light entering said cup-shaped member back through said first and second lens members;
    closure means for closing the open end of said cup-shaped member; and,
    holding means for holding said second lens in place in said cup-shaped member.

2. The construction of claim 1 wherein said first lens portion has a concave inner face provided with a recessed portion.

3. The construction of claim 1 further comprising a first coating layer of a first color provided on said first lens portion concave inner face except in said recessed portion thereof in order to simulate the iris of the eye, and a second coating layer of a second color provided on said first lens portion concave inner face recessed portion to simulate the pupil of the eye, said second coating layer being translucent to allow light to penetrate said second lens member and be reflected off said reflecting means.

4. The construction of claim 3 wherein said first color is gold provided with flecks of brown and wherein said second color is white.

5. The construction of claim 1 wherein said cup-shaped member includes a cylindrical portion of a larger diameter than said first lens portion.

6. The construction of claim 1 wherein said closure means includes a layer of putty material for closing the open end of said cup-shaped member, wherein said holding means includes a layer of putty material around the side edge of said second lens member, and wherein said reflecting means is a layer of reflective material provided on an inner surface of said second lens member.

7. The construction of claim 1 wherein said closure means includes a disc-shaped mirror which closes the open end of said cup-shaped member and wherein said reflecting means is a layer of reflective material provided on said mirror.

8. The construction of claim 7 wherein said holding means is a disc member having a centrally disposed aperture, said disc member being secured inside said cup-shaped member adjacent said first lens portion, said second lens member being secured to said disc member in a relationship overlying said centrally disposed aperture thereof.

9. A simulated eye construction comprising:

a generally cup-shaped body having an inner cavity provided with a light reflecting surface;

a transparent first lens member, having a convex outer face and an inner face, secured to said body at the entrance thereof to close said cavity;

a second lens member which is positioned adjacent to said first lens member;

a first coating layer of a first color provided on said inner face of said first lens around the periphery thereof in order to simulate the iris of the eye; and, a second coating layer of a second color provided on said first lens inner surface radially inwardly of said first layer to simulate the pupil of the eye, said second coating layer being translucent to allow light to penetrate said lens member and be reflected off said body light reflecting surface.

10. The construction of claim 9 wherein said body light reflecting surface comprises a light reflecting layer coated on said body inner cavity.

11. The construction of claim 9 further comprising a disc member having a centrally disposed aperture, said disc member being positioned adjacent said first lens, said second lens member being secured to said disc member and overlying said centrally disposed aperture thereof.

12. The construction of claim 9 wherein a rear surface of said cup-shaped body is convex.

13. The construction of claim 9 wherein a rear surface of said cup-shaped body is defined by a planar disc-shaped mirror.

14. The construction of claim 9 wherein a rear surface of said cup-shaped body is concave.

15. The construction of claim 9 wherein said first color is gold with flecks of brown and wherein said second color is white.

16. A simulated eye construction comprising:
a first lens member having a convex outer surface;
body means for holding said first lens member;
a second lens member held in said body means;
reflecting means positioned in said body means behind said second lens member for reflecting at least some of the light entering said first and second lens members back through them;
a first coating layer of a first color provided on a surface of said first lens member; and,
a second coating layer of a second color provided on a surface of said second lens member, said second coating layer being translucent to allow light to penetrate said lens member and be reflected off said reflecting means.

17. The construction of claim 16 wherein said first lens has a teardrop-shaped recessed portion on the inner surface thereof simulating the pupil of a fish eye.

18. The construction of claim 16 further comprising a disc member having a centrally disposed aperture, said disc member being secured to said body means, said second lens member being secured to said disc member in a relationship overlying said centrally disposed aperture thereof.

* * * * *